United States Patent [19]

Datar

[11] Patent Number: 6,008,040
[45] Date of Patent: Dec. 28, 1999

[54] PROCEDURES FOR EFFICIENT SEPARATION OF CELLS, CELLULAR MATERIALS AND PROTEINS

[75] Inventor: Rajiv V. Datar, Plainsboro, N.J.

[73] Assignee: Synosys, Inc., New Brunswick, N.J.

[21] Appl. No.: 08/676,062

[22] Filed: Jul. 5, 1996

Related U.S. Application Data

[60] Provisional application No. 60/000,952, Jul. 7, 1995.

[51] Int. Cl.$^6$ ........................... B01D 24/00; B01D 37/00; C12N 5/02; C12N 5/08
[52] U.S. Cl. ........................ 435/325; 210/255; 210/600; 210/767; 435/239; 435/243; 435/308.1; 435/814; 435/261; 435/372
[58] Field of Search ........................ 210/600, 601, 210/610, 767, 255; 435/173.9, 239, 261, 308.1, 814, 325, 243, 372

[56] References Cited

U.S. PATENT DOCUMENTS

| | | | |
|---|---|---|---|
| 3,492,396 | 1/1970 | Dalton | 424/12 |
| 4,230,635 | 10/1980 | Senyei et al. | 260/556 A |
| 4,247,298 | 1/1981 | Rippie | 422/68 |
| 4,363,634 | 12/1982 | Schall | 23/230 |
| 4,603,109 | 7/1986 | Lillo | 435/41 |
| 4,617,124 | 10/1986 | Pall et al. | 210/638 |
| 4,619,904 | 10/1986 | Giaver et al. | 436/518 |
| 4,787,971 | 11/1988 | Donald | 210/198.2 |
| 4,880,548 | 11/1989 | Pall et al. | 210/767 |
| 4,925,572 | 5/1990 | Pall | 210/767 |
| 4,963,265 | 10/1990 | Okarma et al. | 210/638 |
| 4,976,861 | 12/1990 | Pall | 210/508 |
| 5,022,988 | 6/1991 | Okarma et al. | 210/321.84 |
| 5,215,926 | 6/1993 | Etchells, III et al. | 436/501 |
| 5,229,012 | 7/1993 | Pall et al. | 210/767 |
| 5,240,856 | 8/1993 | Goffe et al. | 435/299 |
| 5,468,847 | 11/1995 | Heilmann et al. | 530/413 |
| 5,514,340 | 5/1996 | Lansdorp et al. | 422/101 |

OTHER PUBLICATIONS

Wysocki et al, "Planning for lymphocytes: A method for cell selection", *Proc. Natl. Acad. Sci.* USA, vol. 75, No. 6, pp. 2844–2848, Jun. 1978.

Wigzzell et al, "Cell Separation on Antigen–coated Columns", J. Exp. Med., 129:23–36, 1969.

Sofer et al, *Practical Chromatograophy*, Wiley, 1989, pp. 23–36.

Sandrin et al, "Anti–pig IgM antibodies in human serum react predominately with Gal($\alpha$1–3)Gal epitopes", *Proc. Natl. Acad. Sci.* USA, vol. 90, pp. 11391–11395, Dec. 1993.

Rutishauser et al, "Mechanisms of Adhesion among Cells from Neural Tissues of the Chick Embryo", *Proc. Natl. Acad. Sci.* USA, vol. 73, No. 2, pp. 577–581, Feb. 1976.

Perry et al., *Chemical Engineers Handbook*, Section 5, McGraw-Hill, 6$^{th}$ Edition, 1984, pp. 5–23 to 5–29.

Hermanson et al, *Immobilized Affinity Ligand techniques*, Acad. Press, 1992, pp. 231–234.

Datar, "A comparative Study of Primary Separation Steps in Fermentation", Ph.D. Thesis, The Royal Institue of Technology, Stockholm, Sweden, 1986.

Bird et al, *Transport Phenomena*, John Wiley & Sons, 1960, pp. 197–201,411–413, and 643–649.

Antoine et al, *Immunochem.*, "Lymphoid Cell Fractionation on Magnetic Polyacrylamide–Agarose Beads", vol. 15, pp. 443–452, 1987.

*Primary Examiner*—David M. Naff
*Assistant Examiner*—Deborah K. Ware
*Attorney, Agent, or Firm*—Law Offices of John A. Parrish

[57] ABSTRACT

A process and device are provided for achieving cascade flow to achieve rapid separations of target components from fluid mixtures is provided. The devices of the invention have a cascading flow channel. The separation processes of the invention may include singly or in combination, the step of adjusting the total voids volume in all elements employed in the devices of the invention to be equal to or less than 6% of the total volume of fluid that is to be processed. A single separation process or a combination of separation processes may be used where the fluid mixture is whole blood, whole blood that is diluted or is in some other way treated, concentrated, divided into two or more streams, or augmented with blood or blood components, cellular materials such as proteins, antibodies, enzymes and fractions thereof, and nuclear materials such as DNA, RNA and their fragments. These separation processes of the invention provide higher yields and purities of the desired products than has been possible by the prior art.

13 Claims, 5 Drawing Sheets

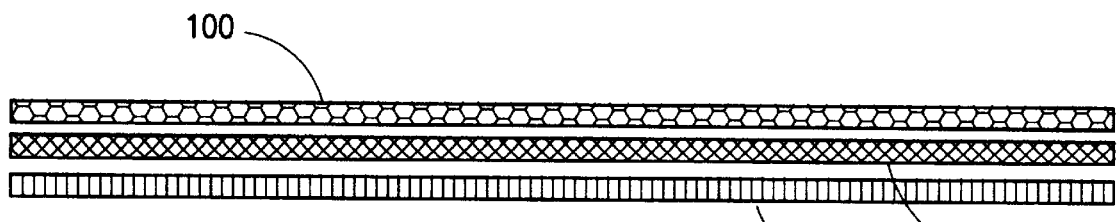
FIG. 9
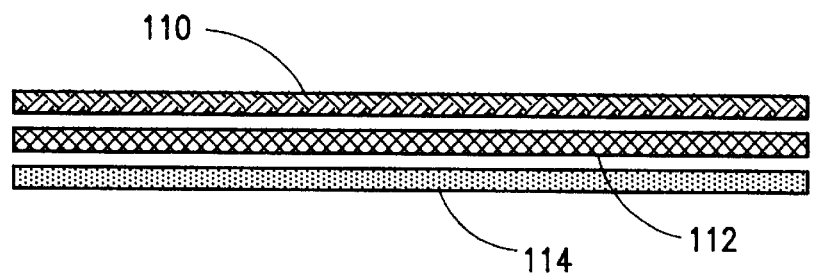
FIG. 10
FIG. 10A
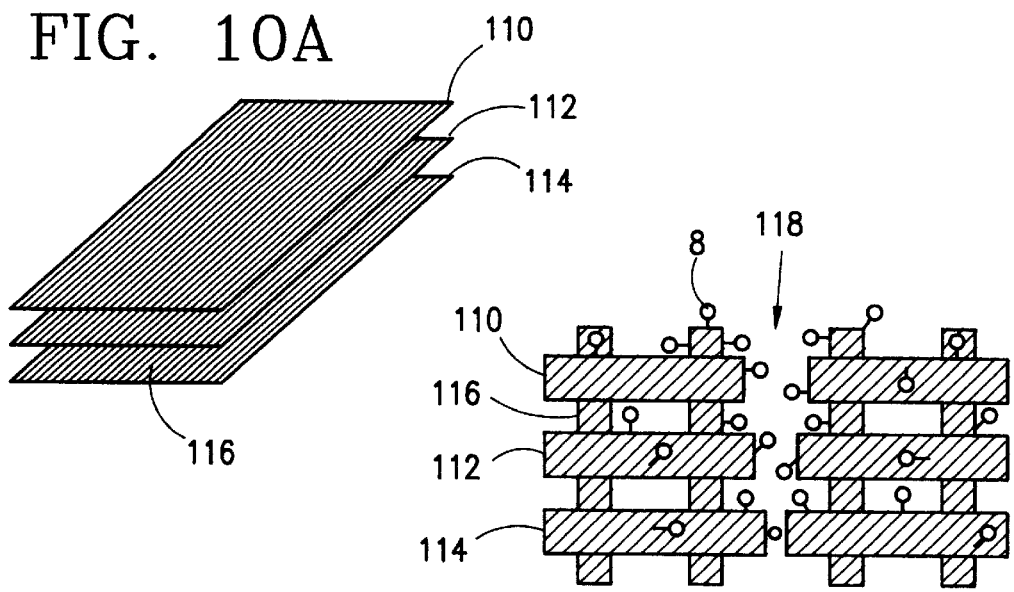
FIG. 10B
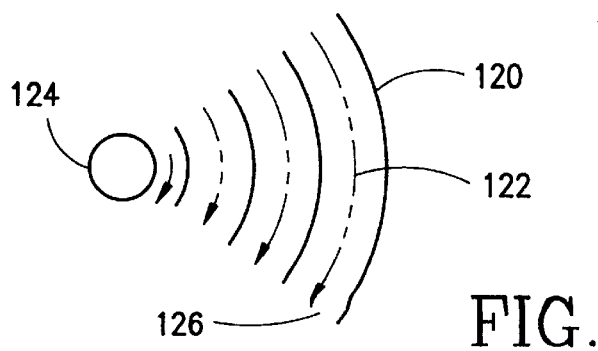
FIG. 10C

PROCEDURES FOR EFFICIENT SEPARATION OF CELLS, CELLULAR MATERIALS AND PROTEINS

This application claims the benefit of U.S. Provisional Application No. 60/000,952 filed Jul. 7, 1995.

FIELD OF THE INVENTION

The invention relates to affinity enhanced, size-gradient selection processes for separating materials such as cells, from a complex mixture of biological materials, and devices for performing those separations. The invention particularly relates to affinity enhanced, size-gradient selection processes, with or without affinity enhancement, for separating materials such as cells, from a complex mixture of biological materials, and devices for performing those separations.

BACKGROUND OF THE INVENTION

Efficient separations of certain types of cells from complex mixtures has important applications in blood and blood component transfusions, cancer therapies, auto immune diseases and diagnostics. Cell separation devices employed in these separations have been used in extracorporeal circuits to selectively isolate, augment and/or reintroduce to the host a specific subset of cells. Separation processes may be used to remove a subset of cells from the mixture of interest ("negative selection") or to prepare a specific subset of interest from a mixture (positive selection). In negative selection, the cells to be discarded remain in the device. In positive selection, desired cells initially remain in the device while the undesired cells and other contaminants flow through and are removed. The desired subset is subsequently obtained as a more pure fraction from within the device.

Blood and lymph fluids provide the medium through which red blood cells, white blood cells (leukocytes), nutrients, metabolites, growth factors, hormones, antibodies, and the like are transported from one site in the body to another to enable production of various compounds by cells and tissues for regulation of other cells and tissues. Additionally, these same fluids remove waste materials to prevent the accumulation of harmful compounds. Blood and lymph fluids also transport cells of the hematopoietic system throughout the body to allow fulfillment of a variety of functions. At the same time, a wide variety of materials are transported to the cells of the hematopoietic system for processing or for inducing a cellular response, as in the case of formation of antibodies to counteract antigens, pathogens, and the like. Thus, interaction between hematopoietic cells and blood can provide useful information about the disease-states in individuals, creating significant interest in the potential therapeutic value of accessing these fluids to manipulate various components related to or present in the blood stream.

Blood is a complex mixture that is known to change in response to foreign environments. When blood or components thereof are not intended for reuse, this may not pose any problems. However, when blood or components thereof have to be returned to the host, such changes could be detrimental. For example, in plasmapheresis or transfusion therapy, it is desirable to restore a person's blood. However, due to uncertainties concerning the safety of the blood supply due to viruses such as cytomegalovirus (CMV), hepatitis, HTLV-1, HIV, or the like, such return to the host may be precluded.

Transfusion of packed cells or whole blood containing donor leukocytes to a recipient can be harmful. For example, transfused leukocytes can cause Graft versus Host (GVH) disease in which the transfused leukocytes cause irreversible damage to the blood recipient's organs in immuno compromised patients. Red cell transfusions can adversely affect the survival of patients undergoing colo rectal cancer surgeries. This effect is believed mediated by the transfusion of components other than donor red blood cells including the donor's leukocytes. At a recent meeting of the American Association of Blood Banks (ABBE Meeting, Florida, 1993) studies were presented which showed that patients who received leukocyte depleted blood, when compared to those who did not, had fewer returns to the hospital following a surgical procedure.

Known cell separations involve several techniques, some of which are based on specific affinities. Other cell separation techniques rely on more serendipitous mechanisms such as entrapment of target cells in supports of various origins and structures. See, for example, Wigzell and Anderson, *J. Exp. Med.* 129:23–36, 1969; Rutishauser et al. *Proc. Natl. Acad. Sci.* 70, 1973; Wysocki and Sato, *Proc. Natl. Acad. Sci.* 75:2844–2848, 1978; Antoine et al. *Immunochem.* 15, 1987. See also, U.S. Pat. Nos.: 4,230,635; 4,363,634; 4,617,124; 4,619,904; 4,880,548; 4,925,572; 4,963,265; 5,215,926; and 5,240,856. The basic process of affinity separation entails creating contact between cell mixtures to be separated and a support matrix to enable the target cells to preferentially attach, bind, adsorb or become trapped to and within the support, and then washing away the undesired cells, or vice versa. Specific affinity techniques use monoclonal antibodies to recognize specific markers on the membranes of cells and to "attract" the target cells to bind to the monoclonal antibodies. Specific affinity "attractions" of target cells also may occur by hydrophobic or hydrophilic interactions, metal-affinities, ion exchangers, and the like.

Given that some form of health care reform in the United States is highly likely, it is of great interest to develop practical and cost-effective procedures and equipment which will enable removal and/or recovery of cells to provide increasingly higher yields and purity levels irrespective of scale. Attempts to scale-up separation procedures, however, have not proven practical. One successful approach to potential large-scale cell separations so far has involved the use of magnetic particles. However, the use of magnetic particles is expensive.

Scale-up beyond laboratory size has involved either columns packed with beads of a particular type and size, with or without specific chemistries, or the use of compressed stacks of membranes. Unfortunately, mechanisms governing the performance of a column packed with relatively uniform packed beads on the one hand, and membranes on the other, are at the opposite ends of the spectrum as to mass transfer rates and capacities. Surprisingly, it is not until my invention that the apparently mutually exclusive parameters described above, have successfully been combined in to one device.

SUMMARY OF THE INVENTION

In accordance with the invention, devices and methods for separating and/or removing target biological cells from a fluid mixture of cells is provided. The invention provides a continuously cascaded tortuous flow path to the fluid mixture through use of biocompatible high surface area packings. One or more specific ligands may be added to these packings to interact with one or more components in the fluid mixture from which the components need separated.

The invention provides a device which has a cascading flow channel. The cascading flow channel advantageously provides a smooth trickling flow of the fluid mixture while providing increased surface area and decreased hydraulic pore diameters of the separation media, as well as increased interaction between the components contained in the fluid matrix and the separation media.

The cascading flow channel employed in the invention provides additional degrees of freedom of operation over the devices of the prior art. For example, if for a specific separation, shear force at the contacting surface between the fluid stream and the separation media is critical for attachment and/or detachment of the target cell to the separation media, the cascading channel enables a desired shear field to be established for a desired flow rate of the fluid mixture through the device. Specific cells can be collected either upstream or downstream of that particular shear field. The cascading channel also can provide continuously changing surface areas to provide improved interaction between the components of the fluid stream and the contacting surfaces of the separation media.

The separation processes of the invention may include singly or in combination, the step of adjusting the total voids volume in all elements employed in the invention to be equal to or less than 6% of the total volume of fluid that is to be processed. A single separation process or a combination of separation processes may be used with biodegradable fluids such as, for example, whole blood, whole blood that is diluted or is in some other way treated, concentrated, divided into two or more streams, or augmented with blood or blood components. These separation processes of the invention provide higher yields and purities of the desired cells than has been possible by the prior art.

BRIEF DESCRIPTION OF THE DRAWINGS

FIG. 9 depicts in schematic form the bonding and layering of porous membrane sheets and/or beads to metallic surfaces;

FIG. 10 is another embodiment of the schematic shown in FIG. 9, but without the metallic support structure, whereby multiple layers of porous sheets and membranes may be stacked upon each other; and FIGS. 10A–10C show how the stacked sheets illustrated in FIG. 10 can be utilized in the separation devices of the invention.

DETAILED DESCRIPTION OF THE PREFERRED EMBODIMENTS

Figure 1:
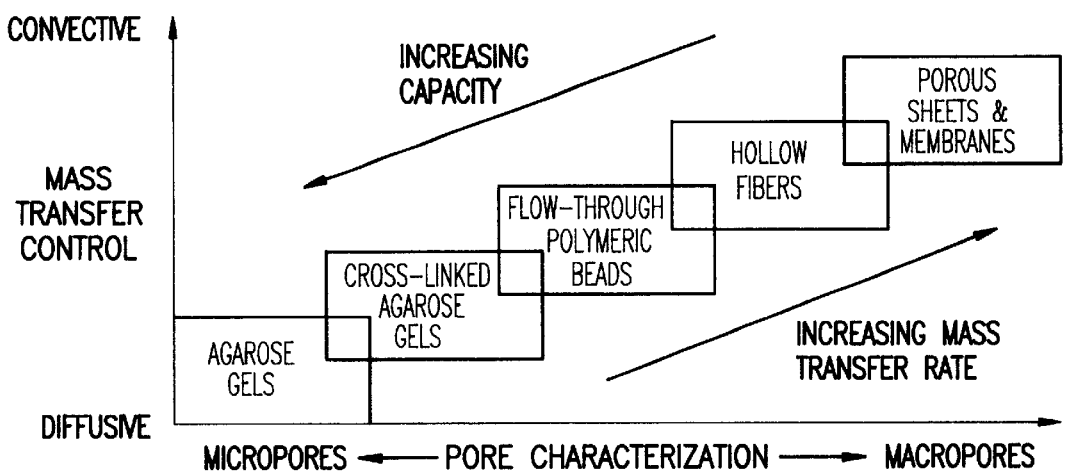
FIG. 1 is a representation of the mass transfer controlling regime, plotted as the ordinate, versus pore character (size and/or diameter), plotted as the abscissa, for known separation techniques.

Methods and apparatus are provided for effecting efficient cell separations. These methods include both cell depletion in which a subset of cells is removed from a mixture of cells, as for example in leukocyte depletion. Other methods include positive selection processes in which a specific subset of target cells is purified from a mixture of cells, as during preparation of pure fractions of CD34+ cells for therapeutic uses. The term "cells" is defined here as including not only those of biological origin, such as from prokaryotic and eukaryotic organisms, but also as including viruses, mycoplasma, and other noncellular particles or components such as those comprising whole or parts of antibodies, antigens, proteins, enzymes, DNA, RNA and various fragments thereof and the like. Cells which remain on contact surfaces of the separation media are referred to as "target cells or particles."

The separation devices of the invention may employ bead columns, porous membranes, porous walled and non-porous walled hollow fibers, and the like. The contacting surfaces in these devices may be formed of any materials known to be useful for separations, including polymers such as polystyrene-divinylbenzene copolymers, polyamides such as Nylon, polypropylene such as low and high density polypropylene, polystyrene, polyesters such as Hirose™, polysulfones, polyacrylonitriles, hydrogels such as polyvinyl alcohol, fluoropolymers such as PVDF and PTFE, cellulosics such as cellulose acetate, gels such as agarose, polyacrylamide, and the like, metals such as stainless steel, titanium, nickel, aluminium, magnetic alloys, and the like, ceramics and inorganic materials such as silica, alumina, silicates, and the like, and glasses, used singly or in any combination. Any of these materials may have specific chemistries on their contacting surfaces treated with specific ligands.

During a separation, a fluid stream is directed through a separation device which provides a cascading, tortuous-path trickle bed which employs separation media with high surface contact areas. Interaction between the components of the fluid stream and the contacting surfaces of the separation media enable one or more components of the fluid stream to be separated and/or removed from the fluid stream. The separation media may have contacting surfaces treated with specific chemistries to enhance interaction between the media and the components to be separated from the fluid mixture. The separation process of the invention thus enables change in the concentrations of those components in the fluid stream, or a change in the ratios of those components in the fluid steam. The invention advantageously enables achievement of separated components of increased purity and of greater amounts than can be achieved with devices of the prior art.

As is known, material selection and packing stability, size or diameter of flow passages, contacting efficiency between cells and the contacting surfaces, adsorption or bond strengths, and hold-up volumes affect separation efficiency.
Material Selection and Packing Stability Although much has been written concerning selection of materials for beads and membranes as separation media, a priori selection of materials for a separation is difficult. Practitioners therefore tend to use trial and error to select separation materials which have specific levels of hardness, porosity, surface chemistry, pore size, and the like.

Traditional column separations employ cross-linked agarose-based gels to improve flow rate associated pressure drops. Cross-linked agarose-based gels are relatively soft gels. Pressure drops therefore tend to be high. The separation capacities of cross-linked agarose gels, however, due to existence of micropores, are usually high. Micropores limit separation speeds because mass transfer is under control of diffusion. Additionally, because soft gels shrink or swell during the passage of different fluids, the overall efficiency of separation is likely to be uneven. Newer polymer-based beads such as those marketed under the trademark Poros by Perseptive Biosystems have attempted to overcome some of the operational problems of soft gels such as agarose-based media.

Membranes are characterized by rapid flow rates at relatively low pressure drops. Internal surface areas in membrane structures are usually lower than in beads, and consequently, capacities tend to be low. Due to their macroporous internal structures, mass transfer is normally convective and quick.

In an attempt to merge the characteristics of gels and membranes, rigid composites where beads have been embedded into membrane-like structures have been employed. These materials are composite microporous sheets such as those available from Amer-Sil S. A., Luxembourg under the trade name Amer-Sil (MPS)™. These materials, however, do not provide a stable, size-gradient matrix bed having continuously cascaded flow channels.

Size or Diameter of Flow Passages

The diameter of a bead and the pore size of a membrane are important determinants of fluid dynamic effects that may occur within a packed bed. These effects include pressure drop, mass-, heat- and momentum transfer, and shear rate. U.S. Pat. No. 5,215,926 attempts to teach that by controlling the mixing (or shear) rate in a vessel where a mixture of cells are in relative motion to the affinity contacting surfaces, the cells can either be attached or detached from their affinity ligand on the contacting surface depending on interaction of the shear rate and strength of the affinity bond. However, prediction of local effects of shear is extremely difficult.

In the stable matrix devices of the invention, a fluid mixture moves relative to a stable matrix which has defined cascading flow channels. Nuclear magnetic resonating (NMR) techniques may be employed to assess and map the void volumes at different cross-sections of the matrix. Once mapped, at any given superficial flow rate (volumetric flow rate divided by cross-sectional area of flow—$cm^3$/minute/$cm^2$ or cm/minute), the average shear rate in the voids at that cross section is easily calculated by known formulas. Control of shear rates along the cascading flow channels then is possible in accordance with the invention.

Contact Efficiency

Contact efficiency may be defined as the level of adequacy required to bring the target cell and the separation matrix into sufficient proximity whereby, if there were an affinity ligand on the contacting surface, and sufficient time were provided for the interaction, the target cell would attach itself to the ligand. Due to low diffusion rates of cells in the liquid component of the fluid mixture, cells must rely on convective transfer for transport to the vicinity of the ligand or, if in an adsorption process, directly to the contacting surface. While diffusion rates of cells in the liquid component of the fluid mixture are small enough to be ignored, this may not be true with smaller particles such as viruses, proteins, and the like.

The invention provides a device which employs macroporous cascading channels for convective transport, while simultaneously allowing the specific area ($m^2$/gm) of the contacting surface to gradually increase along the flow path to effect separations of a variety of target cells.

Adsorption or Bond Strengths

Equilibrium binding constants vary from $10^9$ to $10^{18}$ per mole, typically about $10^{15}$ per mole. Equilibrium binding constants depend on factors including cell type, the affinity ligand, immobilization techniques, concentration of biding sites, and the like. The concentration of binding sites is directly related to the surface area available. A concern in the art is the extent of non-specific binding to the affinity contact surface which might decrease the concentration of binding sites. Several means are known to reduce this undesirable effect. The majority of these techniques relate to the properties of the contacting surfaces. Since shear can affect adsorption, the defined flow channels in devices of the invention permit the accurate transfer of shear effects from the bulk flow rate of the fluid mixture, to the contacting surface. Factors of ligand density, material characteristics of the contacting surfaces, viscosity, and the like, also can play significant roles.

Hold-up Volumes

Hold-up volumes in devices and equipment of the art typically have about 5% of the original fluid volume. This is important because if fluid purging is not permitted, then the hold-up volume is a loss. However, hold up volume is applications dependent, and can vary from 3% to 10%.

Membrane-based systems tend to have higher hold-up volumes due to their higher porosities, whereas bead columns operate at lower porosities and thus have lower hold-up volumes. Since the cascade matrix structure of devices employed in the invention varies along the path of flow of the fluid mixture in the device, the devices of the invention can produce a hold-up volume that satisfies the competing requirements of porosity and capacity.

Description of Process and Device

To further understand the invention, reference is made to the drawings. FIG. 1 schematically illustrates the relative operating characteristics and regimes of prior art methods. These methods depend on mechanisms such as convection and/or diffusion which affect mass transfer on pore characteristics of the separation media.

At one end of the separation spectrum are slow separation processes which rely on diffusion and adsorption. These processes are exemplified by chromatography which relies on "soft" gels such as agarose. Agarose-based materials have predominantly submicron-to-micropores. These materials depend primarily on diffusion to achieve separations of target cells such as proteins. Since proteins must "diffuse" through the small pores of the Agarose material, mass transfer is very slow. Several hours therefore may be required to achieve a particular separation.

At the other end of the separation spectrum are rapid processes which employ membranes and porous sheets characterized by very high porosities. These macroporous materials permit fluid mixtures to flow rapidly through the material at low pressure drops. This causes convective transport of materials in the fluid stream to sites where target cells can be trapped by the mechanisms described above. A known separation process that attempts to combine the two extreme separation processes mentioned above employs polymeric flow-through beads such as POROS™ from Perseptive Co. and HYPER-$^{DAM}$ from Biosepra Co. Unfortunately, this compromise process results in only average separation capacities.

Surprisingly, it was not until my invention that a device which successfully combines the characteristics of the techniques shown in FIG. 1. was achieved. This device employs a combination of beads, gels, sheets, membranes, and the like, sandwiched and/or arranged together in any order and number, to provide a cascaded flow.

Figure 2:
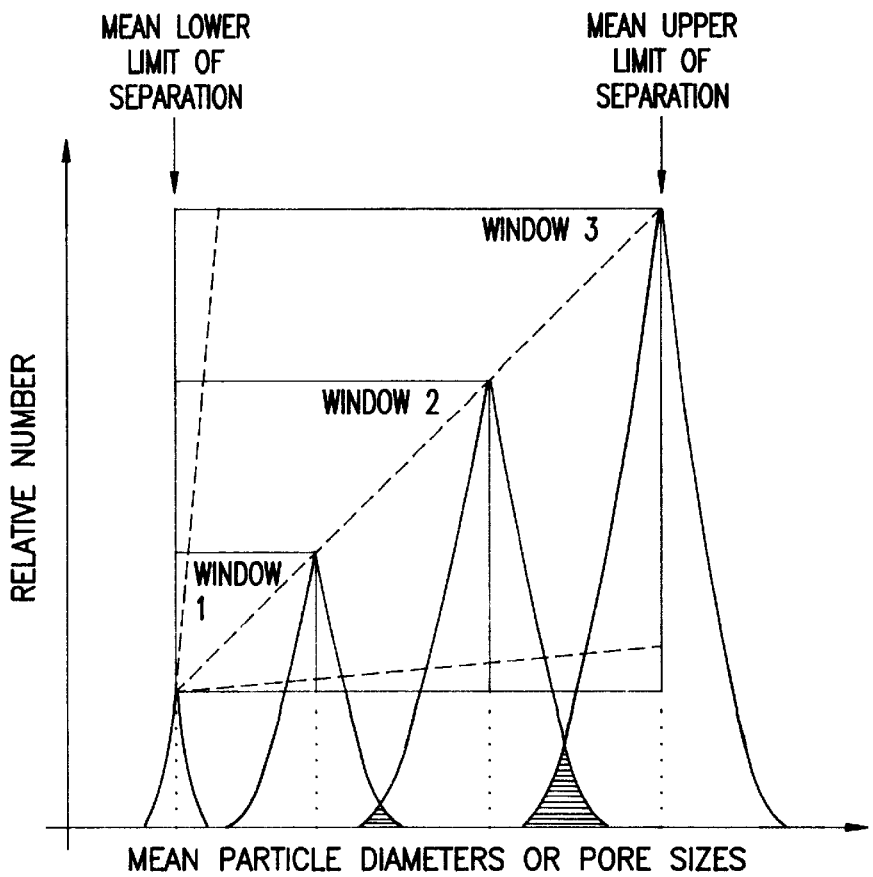
FIG. 2 is a representation of the operating windows available in a cascaded device of the invention as a function of the mean particle diameter or pore size of the packing material of the separation media.

FIG. 2 illustrates the flexibility which the cascade, and size-gradient devices of the invention provide. Typically for a mixture of cell sizes and shapes, an upper limit of separation is chosen. The contacting surfaces of the separation media employed in the device may be in any form. Depending upon whether beads or porous sheets are selected as the separation materials, those material are associated with a selected particle diameter or pore size distribution as shown in FIG. 2. The size of contacting surfaces can be selected to remove target cells at the mean upper limit of separation, i.e. the mean upper limit of separation shown in FIG. 2. The size of contacting surfaces also can be selected to remove target cells at the mean lower limit of separation shown in FIG. 2. Between the upper and lower limits of separation are structures that provide a successive grading in size of the contacting surfaces of the separation media.

Three windows of operation are shown in FIG. 2. The diagonal line (hereafter called operating line) that transects all of the windows shown in FIG. 2 represents the loci of points which connects the peaks of the mean particle diameters or pore sizes of the separation media selected. Thus, for example, the invention may be tailored to include four types of separating structures and remain in Window #1, or two separating structures and remain in Window #3. The slope of the operating line enables additional degrees of freedom of separations which have previously been unavailable in separation devices. For instance, the slope of the operating line gradient (or cascade) may be extremely shallow (slope tending towards zero), or extremely steep (slope tending to infinity). Additionally, the loci of points can be two or more straight lines of different sloops such as convex, concave, sinusoidal or of whatever shape necessary to define a particular separation, so long as a cascade or size-gradient is defined. The contact structures also may be sandwiched as any combination of beads and porous sheets or membranes, each and in combination, to provide a variety of separation mechanisms. These structures may be chemically activated individually or in any combination by specific chemistries to enhance separation.

As a non-limiting example, an illustration of negative selection wherein leukocytes are separated from whole blood or packed red cell concentrates is discussed. Leukocytes, together with a wide variety of components are present in blood in a wide variety of sizes. For instance, gel-like aggregates may be in blood in sizes which vary in size up to about 200 micrometers. Leukocytes range from macrocytes and granulocytes, typically between 15–20 micrometers, to lymphocytes which are in the 5–7 micrometer and larger range; together, these represent the major proportion of all the leukocytes in normal blood. Red blood cells are typically 7 micrometers in diameter, which in size is between the two major blood components to be removed. Additionally, all of these cells are able to deform so as to pass through much smaller openings than their normal size, as is the case of flow in capillary blood vessels. Simple sheets of filters compressed together, due primarily to their inherently high porosity which is inversely proportional to capacity, therefore can not provide the "depth-capacity" necessary for high-efficiency removal of leukocytes. Where devices and processes which use beads of a uniform type and size are employed, a relatively larger surface area for attachment and/or entrapment is available, but this has the disadvantage of making selectivity based on pore size differences and the associated lack of control of the fluid dynamics of the separation. In negative selection, all known devices and processes for leukocyte separation use compressed fibrous sheets and/or membranes. This results in two consequences: (1) the amount of removal of leukocytes is not very high, typically between 10–1,000 fold (i.e., 1–3 log) relative to incident amounts; and (2) the capacities of these known devices are only about one bag (or unit) of blood (nominally 450 mL volume). The invention, however, can achieve amounts of leukocyte removal of between 10,000–100,000 fold (or 4–5 log), while simultaneously able to process larger amounts of blood.

In accordance with this aspect of the invention, an upper size limit of separation is chosen to correspond to use of gel aggregates, i.e., about 200–300 micrometers. A lower limit of size separation is chosen to permit passage of red blood cells, i.e, about 6–6.5 micrometers. Depending upon degree of purification desired, hold-up volumes, capacities, and the like, the types and compositions of the sandwiched layers of separation media are selected as described above to achieve a desired level of separation. Any one or all of the individual layers of separation media that form the cascade separation device of the invention can be treated according to known methods with specific chemistries to enhance separation.

In positive separations where target cells are bound to the contacting surface and then released from the contacting surface to form the desired separation product, the cascade mechanism enables independent selection of the operating line and window. Thus, when target cells vary greatly in size, a shallow operating line can be selected. In separations where target cells are within a narrow size range, a steep operating line can be chosen. Increased separation specificity may be achieved by treating the separation media with specific chemistries to enhance retention of target species while allowing undesired cells to pass through the separation device.

Figures 3, 4:
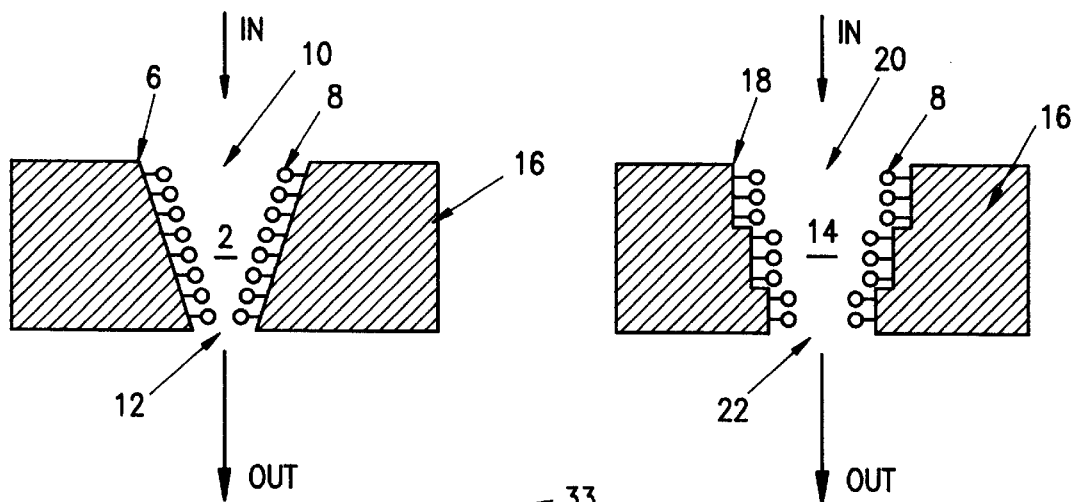
FIG. 3 is a schematic of an idealized, cascading flow channel according to the invention.
FIG. 4 is a schematic of an idealized, non-continuous cascade or stepped flow channel according to the invention.

FIGS. 3 and 4 show cross-sectional views of idealized flow channels for flow of fluid mixtures through the cascading matrices of the invention. FIG. 3 represents an infinite cascade (a conical section), while FIG. 4 represents a stepped cascade. Flow channels 2 and 14 are defined by selection of various matrix layers 4 and 16, respectively. One of major fluid ports 10 and 20 has a larger diameter than minor ports 12 and 22. The ratio of diameters of the major port to the minor port is determined as described above by selecting the operating window and the operating line for a particular separation. Chemical and/or biological moieties 8 may be bound to contacting surfaces 6 and 18 within the flow channels. These moieties can be used to confer specific chemistries to the channels to attract target cells. Surfaces 6 and 18 vary as to amount of surface area available for entrapment of target cells and attachment of chemical moieties such as ligands. The stepped cascade system of FIG. 4 provides a larger surface area to which proportionately more ligand may be bound, thereby providing greater separating capacity.

To illustrate, where fluid flows from larger port 10 to minor port 12, then for any given flow rate, fluid shear is lower at larger port 10 and higher at minor port 12. Fluid shear is automatically graded in accordance with the shape of the cascade, i.e, continuous as shown in channel 2 of FIG. 3 or stepped as shown in channel 14 of FIG. 4. Thus, in absence of specific chemistries in the separation channels 2 and 14, then when a fluid mixture of cells of varying sizes enters major port 10 or 20, then successively smaller cells can pass deeper into flow channels 2 or 14, while larger cells sizes are trapped in the channel. The diameter of minor ports 12 and 22 thus can be chosen to permit passage of selected size ranges of cells to pass through the separation device of the invention. When specific chemistries optionally are employed in cascading flow channels 2 and 14, two mechanisms can be utilized to achieve separations: (1) absence of flow at solid surfaces; and (2) negligible diffusivity of cells into the contact surfaces of the flow channels. Thus, the invention enables use of convection to cause cells to achieve close proximity to activated surfaces 6 and 18 for separation. Since the flow rate at contacting surfaces 6 and 18 is nearly zero compared to the bulk flow rate in the middle region of channels 2 and 14, this enables sufficient contact time between the target cells and the chemical moiety, or ligand to be achieved to cause the target cells to bind to the chemical moieties or ligands 8. When undesired cells are washed away either in the direction of flow, or by flow reversal, the target cells can be eluted or removed by known methods such as changing the chemistry of the elution fluid, flow rate, or its reversal.

Figure 5:
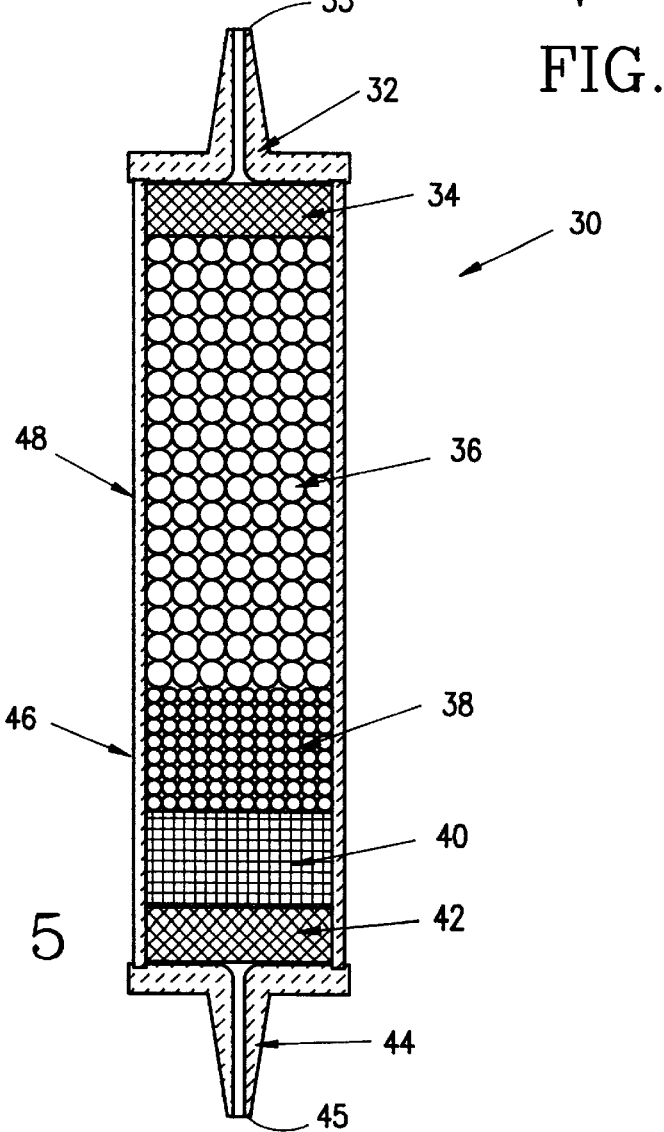
FIG. 5 is a cross-sectional elevation of a device according to the invention.

FIG. 5 shows a cross-section of an embodiment of the device of the invention. Device 30 is cylindrical, having top cap 32 including inlet orifice 33, bottom cap 44 having outlet orifice 45 and cylinder 46 for defining chamber 48. Beads 36, 38, and 40 are packed into chamber 48. First and second porous members 34 and 42 are mounted at the top and bottom of chamber 48 to retain beads 36, 38 and 40. Depending upon the specific separation, the flow rate and capacity of cylinder 46 may be varied. Cylinder 46 may have a high aspect ratio (h/d) of height(h) to diameter (d) where h/d is more than 1, or a low aspect ratio where h/d is less than or equal to 1. The devices of the invention can be constructed in various shapes such as squares, rectangles, triangles, and the like. The devices of the invention may be assembled with biocompatible plastic materials in, for example, top cap 32, bottom cap 44 and cylindrical tube 46. Cylinder 46 may be opaque, or transparent to permit viewing the internal flow and processing of fluid mixtures as they pass through the separation device. Materials employed for porous member 42 and porous member 34 may be, for example, polyphthalate carbonate, polycarbonate, polysulfone, nylon, polyvinylidenefluoride (PVDF) (e.g. Porex® Technologies, Fairburn, Ga.), polybutylene terephthalate and/or polyvinylchloride (PVC) composites preferably include BioPor(PBS)™ products Synosys, Jungfahr (Austria). Porous members 34 and 42 may be activated with specific chemistries by methods known in the art to attract specific target cells in the fluid stream.

Top cap 32 and bottom cap 44 conveniently can be provided with grooves for accepting mating surfaces of cylinder 46 whereby portions of caps 32 and 44 can overlap cylinder 46 as shown in FIG. 5. Bottom porous member 42 is force fitted into cylinder 46 until member 42 contacts cap 44. Alternatively, bottom porous member 42 may be formed as an integral part of bottom cap 44. Bottom porous member 42 has sufficiently low porosity to prevent passage of beads 40.

Packing of cylinder 46 with beads such as beads 40, 38, and 36 in chamber 46 is performed in accordance with known methods such as those employed in chromatography. Accordingly, beads 40 are suspended in a compatible carrier solvent (e.g. water) to form a slurry. The slurry is slowly poured into cylinder 46 from the top of cylinder 46, i.e, that portion opposite bottom cap 44. During pouring, a vacuum is drawn through orifice 45 of bottom cap 44 to remove the carrier solvent and to enhance compaction of beads 40 against bottom porous member 42. After beads 40 are compacted against porous member 42, layers of beads 38 and 36 similarly are formed against beads 40. Porous member 34 then can be interference or force fitted into cylinder 46. Alternately, porous member 34 can be constructed to be an integral part of top cap 32. The mean pore size of porous member 34 is selected so that beads 36 cannot pass through porous member 34. Assembly of device 30 is completed by fitting top cap 32 having an inlet orifice 33 onto cylinder 46. Sterile, air permeable Teflon plugs, not shown, may be fitted between to any of top and bottom caps 32 and 44, and porous members 34 and 42 within cylinder 46 to vent air from device 30 prior to use.

During use of device 30, a fluid mixture of, for example, cells and proteins enters inlet orifice 33 in top cap 32 and flows through porous member 34. Particles and macro aggregates which are larger than the pore size of porous member 34 are retained by and within porous member 34. Activation of the internal surfaces of porous member 34 by specific chemistries may be performed in accordance with methods known in the art to enhance removal of target particles or cells.

The fluid mixture, after passage through porous member 34, enters beads 36. Beads 36, having a larger size than beads 38 and 40, permits rapid flow of the fluid mixture at low back pressure while simultaneously entrapping larger cells in and around beads 36. Entrapment may occur by a combination of impaction and interception by the cells onto the contacting surfaces of beads 36. Beads 36 may be treated with specific chemistries as known in the art to enhance removal of target cells and particles.

As the fluid cascades downwardly through chamber 48, successively smaller target cells are retained within interstices between beads 36, 38, and 40 as well as porous member 42 by one or all of the mechanisms previously stated. The separation product then passes through bottom cap 44. The separation product, if a negative separation is employed, will be greatly diminished in target cells. If a positive separation is employed, the separated product will be greatly enhanced in target cells.

In another embodiment of device 30, sections of beads 36, 38 and 40 may be provided as individual porous capsules which can be removed from within the device. These capsules may be covered with biocompatible material such as silicone, Teflon™, and Porex™. Each capsule may be evaluated for the matter trapped and/or bound to the beads in the capsule. This would be advantageous where positive selection has to be combined with a long, shallow operating line where multiple bead sections may be required and where target cells are desired to be bound or trapped in the middle section(s) of beads, such as beads 38, to provide increased purity in the separation product. The relative proportions of beads 36, 38 and 40 shown in FIG. 5 may vary over wide limits. Selection of the amounts of beads 36, 38 and 40 may be readily determined by those skilled in the art in accordance with the needs of a particular application, capacity, hold-up volume, and the like.

Additional equipment can be employed with the device. For example, if not under gravity feed, then a pump or some other mechanism may be used to move the fluid from a starting source, through the device and its various chambers and conduits, and to a return or a collection source. Other materials, components and/or treatments complementary to the devices of the invention, may include centrifugation, precipitation, extraction, filters, absorption, chemicals, radiation, sterilization, and the like. Integrated process control systems which monitor and detect process variables such as flow rate, pressures, temperatures, air bubbles and the like, for the purposes of automating the entire operation, may also be associated with the device.

Beads 36 may be formed from, for example, 200 $\mu$m cross-linked agarose, beads 38 may be formed from 20 $\mu$m polystyrene, and beads 40 may be 6 $\mu$m high-performance silica beads. Porous member 34 may be formed from 200 $\mu$m PVDF POREX™ and porous member 42 may be formed from 6 $\mu$m PVDF POREX™.

Figure 6:
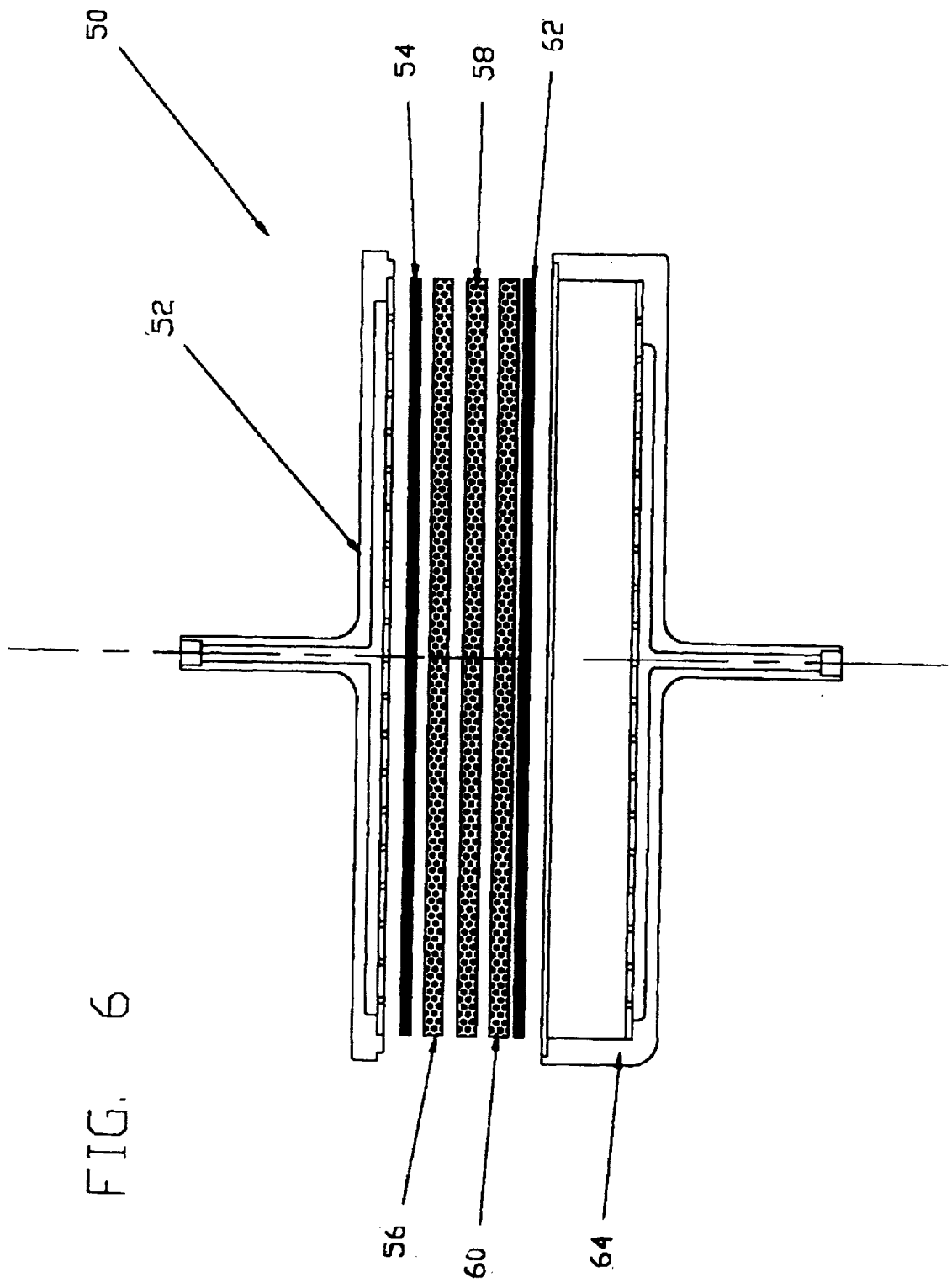
FIG. 6 is a cross-section view of another embodiment of the device according to the invention.

FIG. 6 shows an embodiment of the device of the invention, shown generally by reference numeral 50, which employs a low aspect ratio. Device 50 is useful when the pressure drop across the device needs to be very low, such as when trying to separate anti-bodies from whole blood while allowing passage of other blood components, including whole cells. The larger cross-sectional flow area provided by device 50 also provides reduced clogging since flow per unit area is believed lower than the flow per unit area through devices such as device 30 which has a high aspect ratio. Construction of device 50 is similar to device 30 in that bead slurries can be sequentially deposited.

In a preferred embodiment, as shown in FIG. 6, device 50 includes top cap 52 having inlet orifice 53, bottom cap 64 having outlet orifice 65, and cascaded separation elements 54, 56, 58, 60, and 62. These separation elements may be sandwich constructions of any combination of beads, porous sheets and/or membranes. Bottom cap 64 and top cap 52 preferably are provided with holes whereby suction can be applied to caps 64 and 52 to assist in seating of the layers against each other.

Figure 7:
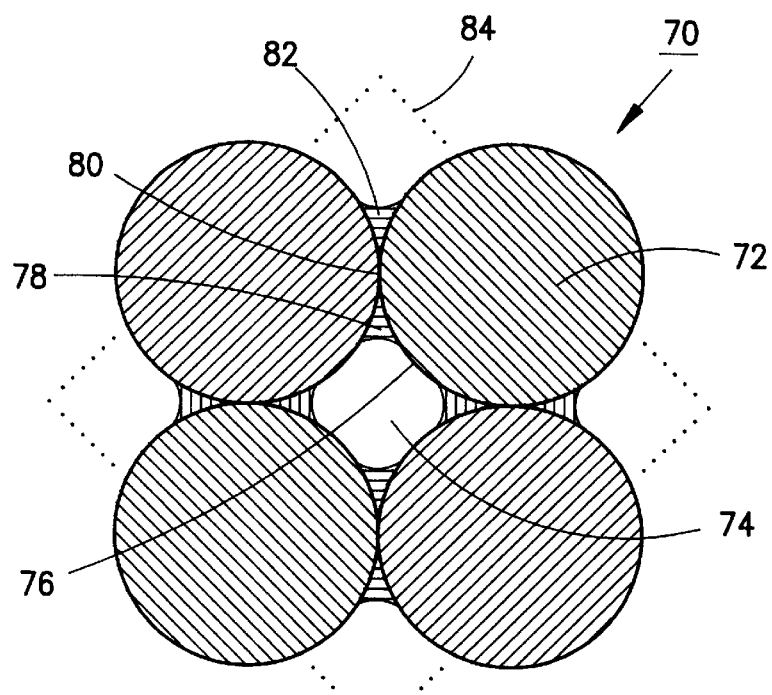
FIG. 7 is a projection of the flow channel formed by four beads in contact with each other in the same plane, and an exploded perspective view of the bonds that can be created between two or more beads to stabilize the packing.

FIG. 7 shows an idealized flow channel 70 that is formed when four solid, spherical beads 72 contact each other in the same plane. A known parameter used to characterize flow channels is hydraulic diameter. Hydraulic diameter is defined as four times the cross section flow rate divided by the wetted perimeter of the channel. See Chemical Engineers Handbook, Section 5, Perry (Ed.), McGraw-Hill, 6th Edition, 1984. Channel 74 in FIG. 7 is defined by arcs 78 of beads 72. The rate of flow of fluid is highest at the center of channel 74, and gradually declines to zero at or close to the contact points 80. Thus, depending on the bulk flow rate through channel 74, mass transfer at the center of channel 74 can be by convection. Mass transfer in regions 82 near contact points 80, however, will be slow and controlled by diffusion. Thus, for the purposes of defining the hydraulic diameter of flow channel 74, it would be convenient to ignore regions 82. The length of each tangent line which defines the cross section of flow 84 is calculated by known methods to be approximately 41% of the diameter of the bead (i.e., for beads with diameters of 100 micrometers, each of the tangent lines has a length of about 41.4 micrometers.). Thus, for a square cross section of flow as defined above, the hydraulic diameter is the same as one of the tangent lines, in this case about 41.4 micrometers. Accordingly, for beads with diameters of 100 micrometers, a solid particle smaller than 41.4 micrometers in diameter will be able to pass through channel 74 created by the beads. Accordingly, by relating the diameter of the beads to the hydraulic diameter of the channels formed by the beads, it is possible to a priori select the bead size required to achieve a particular separation effect.

The primary parameters which determine amount of inter-bead and/or intra-bead bonding are solvent concentrations, temperature and time of exposure. By control of these variables, it is possible to control the size of region area 82 to accurately define the shape of flow channel 74. Flow channel 74 also influences shear rates generated, and which may be important during the passage of cells through the flow channels. Although FIG. 7 illustrates the mechanisms of flow and bed stabilization using beads, other materials such as arrays of fibers with differing diameters for different sections in the device, which define the shapes and sizes of the cascading flow channels also may be used.

Figure 7A:
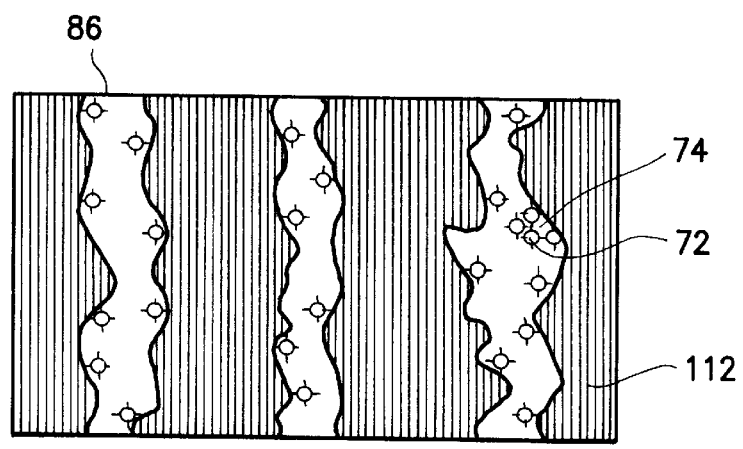
FIG. 7A is schematic of showing clusters of beads embedded in a matrix to create defined flow channels.

Regions 82 in FIG. 7 occur during in-situ bonding of beads into a matrix. Bonding or sintering of small porous or solid beads to each other or into a stable matrix to provide well-defined flow channels can be done in several known ways as described below. Flow channels can be formed by heat pressure sintering, i.e., controlled heating with or without partial melting of ceramic and/or thermoplastic beads into a matrix under applied pressure. FIG. 7A illustrates flow channels which can be made in this way. As shown in FIG. 7A, macroflow channels 86 in the matrix of membrane layer 112 have beads 72 or clusters of beads 74 therein. The applied pressure could be hydraulic or pneumatic wherein fluid pressure is employed to force the beads together. The heat source could be microwave or macrowave energy, which is rapid and accurately controllable, especially when the fluid does not have a high dielectric constant. The fluid movement also can be employed to dissipate unwanted heat.

Solvent bonding also may be employed. Solvent bonding uses a poor solvent to partially dissolve and/or soften the beads to cause them to bond at points of contact. The beads are packed in place, a solvent or solvent mixture added, pressure and perhaps heat applied, and the bonding occurs in-situ. Bead and solvent combinations which may be employed include, for example:

(a) Cellulose acetate beads and acetone-water or acetone-formamide solvent mixtures;

(b) PVDF beads and any of acetone (cold), acetone-water mixtures, triethyl phosphate (cold), dimethyl formamide (DMF) or DMAC solution in water, and isophorone;

(c) Polysulfone or polyether sulfone beads with dilute solutions of aromatic hydrocarbon (toluene) in aliphatic hydrocarbon (hexane) or dilute solutions of DMF or DMAC in water;

(d) Nylon beads with formic acid in water or phenol in alcohol;

(e) Cellulose beads with dilute cuprammonium complex in water.

In-situ polymerization with another polymer formed under mild conditions also may be employed. Non-limiting examples of in-situ polyermization include:

(a) Soaking polyamide beads in a dilute aqueous solution of a diamine or polyamine (ethylenediamine or meta or para phenylenediamine), and then a hexane solution of a multifunctional acid preferably, an acid chloride (adipic acid, isophthaloyl chloride, terphthaloyl chloride) is added.

(b) Polyurea beads: Employing a polyamine in aqueous solution and a polyfunctional isocyanate in non-miscible organic solution;

(c) Polyurethane beads; Employing a polyglycol in aqueous solution and a polyfunctional isocyanate in the organic solution;

(d) In situ polymerization of unsaturated organic compounds such as acids(acrylic, methacrylic), alcohols (vinyl alcohol), esters(acrylates, methacrylates), nitroaromatics (1-vinyl imidazole, 4-vinylpryridine); and (e) In situ polymerization by free radical polymerization using initiators such as 2,2' azobis(2- methylpropiontrile) using energy from UV, e-beam radiation, or heat(either direct or indirect through micro-and macro-wave heating).

Because in-situ polymerization can coat the entire bead with the additional polymer, this technique can be used to create unique coatings to which special chemistries can be subsequently attached and/or be able to use starting beads that may be more variable in size distribution, weight characteristics, and the like. In addition to the above-described methods, the integral cascaded matrix can be produced by, for example, radiation treatment, Devices which use cascaded matrices formed by this or similar alternatives are within the scope of this invention.

Figure 8:
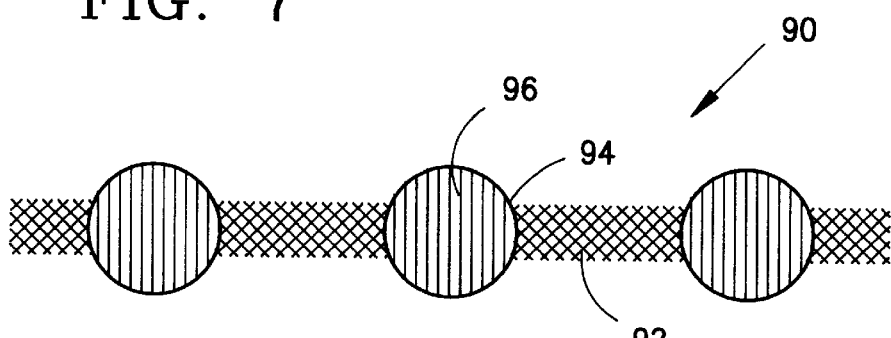
FIG. 8 is a schematic of beads chemically and/or physically embedded into and/or on the surfaces of an open web structure according to the invention.

FIG. 8 shows an alternative means of bead and/or membrane stabilization, whereby beads 96 may be chemically and/or physically embedded within and on the surfaces of open web structure 92 to provide embedded web 90. Matrix stabilization of beads 96 and web structure 92 by chemical bonding 94 may include one or all of the previously discussed methods used singly or in combination. Sheets and or discs of separation media produced as embedded webs 90 can be stacked in various combinations to provide a cascade effect in accordance with the invention. Additional non-embedded beads may be sandwiched between the embedded webs 90.

In another embodiment, embedded webs 90 may be formed as piezoelectric webs. When a piezoelectric material is deformed through application of force or pressure changes, it undergoes a proportionate, reversible re-distribution of electric charge on its surfaces. During the re-distribution of charge, a minute current flows from one surface to the other. The reverse is also true. Thus, application of an external current causes a charge re-distribution which, in turn, causes a physical deformation (i.e., change in length or thickness) of the material. For example, application of an alternating current (ac voltage) will cause the internal structure of the material to vibrate and vice-versa, resulting in generation of highly localized vibrations and/or eddys in the vicinity of the contacting surfaces. Such secondary effects can be employed to modulate the entrapment, binding, adsorption and/or desorption characteristics of the contacting surfaces. Piezoelectric webs useful in the invention include, for example, PVDF.

FIG. 9 is a schematic illustration of a novel method of bonding and layering polymeric materials onto and/or around metals in accordance with the invention. Metallic sub-structure 102 may be formed of metals such as stainless steel, titanium, nickel, magnetic alloys, and the like. Structure 102 may have a wide variety of configurations, preferably flat or spherical, most preferably flat. A flat version of structure 102 may have any desired thickness and geometry, and may include defined channels as in FIG. 9. Alternatively, structure 102 may be formed of sintered metal. If structure 102 is provided as a spherical metal form, structure 102 may have sub-micron, microscopic or macroscopic size pores, and be porous or solid in its internal structure depending upon the target cells. The surfaces of metallic sub-structures 102 are typically roughened by abrasion, particle blasting, chemical or electrochemical etching, or by controlled stretching. Metallic sub-structures may provide advantages of increased density, magnetism and inertness, depending on the specific separation application.

Fiber layers 104 may be permanently bonded to metal structures 102 by epoxy bonding methods known in the art. Fibers 104 may include fluoropolymers such as Teflon® or PVDF coated with low melting fluorinated copolymers (copolymer of PVDF and Teflon®); terpolymers of PVDF, PTFE and hexafluoropropylene. Coatings may be formed from a variety of known low melting polymers, copolymers, and solvent systems.

After fiber layers 104 are bonded to metal sub-structure 102, then secondary (and tertiary) fiber layers 100 may be deposited sequentially in any combination to form a cascade. Layers 100 may include membranes, embedded webs, piezoelectric webs, and beads, examples of which have been described above.

Sub-structure 102 maybe formed of a variety of materials, preferably metal. Fiber layers 104 may be bonded to sub-structure 102 by dielectric heat sources such as microwave or radio frequency energy (macrowaves), either in the pre-treatment stages, or during the bonding, curing and/or drying of the membrane, beads, and fibers to one another, and/or to the metallic sub-structures. Layers thus formed are stable and porous, and are strongly bonded to one another.

FIG. 10 illustrates a layered structure formed of flat, sheet-like porous membrane structures. Top membrane layer 110 typically has a larger pore size than membrane layers 112 and 114 below. The structure of FIG. 10 thus provides cascaded-flow. At an extreme, the pore size of the bottom-most membrane layer 114 may be so small so as to render it impervious to particles and/or liquid. Additionally, each of membrane layers 110, 112, 114 may be hydrophilic or hydrophobic, and may be modified chemically for affinity or otherwise, and used in any combination. Although FIG. 10 shows a three layered membrane structure, it is to be understood that more than three membrane layers may be employed.

FIG. 10A is an exploded schematic view which illustrates a method of stacking membrane layers 110, 112 and 114. These layers, individually or in any combination, may have projections 116 on one or both of their surfaces. Projections 116 may run longitudinally or diagonally on the membrane layer. These projections may be microscopic or up to several millimeters in height and width. Spacing of projections 116 is flexible and depends on the end-use application. For example, when surface area is important, projections 116 have a of very small size, and are spaced close to one another. On the other hand, when surface area is less important and where the device has to treat solid-laden fluid streams, projections 116 can be large and spaced far apart. Projections 116 can be made integral with the membrane layer, or added ex post.

FIG. 10B is an exploded, cross-sectional schematic of multiple sheet arrangement of FIG. 10A. FIG. 10B shows presence of chemical and/or biological moieties 8. Moieties 8 are bound to the contacting surfaces of membrane layers 110, 112, 114 and of projections 116, in a manner as previously described for FIGS. 3 and 4. Moieties 8 confer specific chemistries to attract target cells and/or other target molecules. Spacing of projections 116 provides channels along which the fluid stream flows parallel to the membrane layers.

The porous structure of membrane layers 110, 112 and 114 provide a cascaded structure wherein pore sizes 118 of each layer permits fluid and particles of a size smaller than the average pore size of that sheet to progressively cascade towards the sheet with the smallest average pore size. Pore sizes 118 of each layer in a multiple layer stack can be independently chosen by those skilled in the art to achieve a collective and predetermined size effect in accordance with the invention.

FIG. 10C is another embodiment of a device in accordance with the invention. In this embodiment, shown generally by reference numeral 126, a porous sheet 120 is spirally wrapped around a porous, central core inlet 124 to create outwardly moving flow channel 122. Porous sheet 120 may be a single sheet with projections 116 thereon. Porous sheet 120 also may comprise a highly compacted structure formed of membrane layers 110, 112 and 114 of FIG. 10B, and wrapping that compacted structure upon itself as a "jelly-roll" around central core 124. During operation, a fluid mixture enters central core 124 and flows outwardly therefrom in a spiral manner whereby the fluid mixture exits at the outermost point of device 126. Simultaneous presence of ligand moieties such as 8, a pore size cascade such as 118, and projections such as 116 on porous sheets 110, 112, 114 and/or 120 enable manufacture of an extremely flexible and efficient separation device in accordance with the invention. The devices of the invention will now be illustrated by way of the following examples are for illustration and not by way of limitation.

EXAMPLES 1–6

High Efficiency, Size-gradient Separation of Leukocytes

These examples illustrate the improvements in leukocyte removal over the prior art. There are benefits associated with transfusing blood or its separate components which are diminished in their leukocyte content. These benefits relate both to reduced side effects to the patients receiving transfusions and the resultant reduction in the number of return visits of those patients for treatment. While prior art devices can reduce leukocyte content by about 1,000-fold (or 3-log), there is need to achieve further increases in the extent of removal of leukocytes. It is generally believed that during transfusions that a desired extent of removal is about 6-log (or 1,000,000-fold). Reductions in leukocyte content beyond those levels may be too low to benefit the patient.

One unit of whole blood drawn from a donor in the United States is nominally 450 milliliters (mL) in volume. Whole blood is rarely used unless it is for some immediate therapeutic need. Instead, individual units of whole blood are processed in one of two ways to produce a unit of red cell concentrate, hereafter referred to as packed red cells (PRC). The concentration of red cells (or hematocrit) in whole blood is usually about 38% to 52 Vol. % while that for PRCs the concentration is about 70% to 80 Vol. %. The volume of most PRC units range between 250 to 300 mL.

CPDA-1 is a combination of anti-coagulants and nutrients used to maintain the "effectiveness period" of red cells prior to transfusion. In whole blood or PRC treated with CPDA-1, red cells are resuspended in plasma. In a relatively newer blood product made by what is known as the Adsol process, red cells are first concentrated to almost 100% by volume by centrifugation, depleting almost all of the original plasma. The red cells are then resuspended in a low viscosity physiological or saline fluid that contains preservatives which can increase the effective life by about ten days compared with the CPDA-1 process. On a viscosity spectrum, CPDA-1 PRCs have the highest viscosity, followed by CPDA-1 whole blood, and finally the Adsol product. Despite varying viscosities of the different feed streams, the examples below demonstrate the superior ability of the invention to improve removal efficiencies of leukocytes irrespective of viscosities. This improved removal is achieved by "amplitude dampening" effect of the size-gradient cascade flow channels used in the devices of the invention to "smooth out" the changing viscosity of the fluid stream as it progresses through the column.

The whole blood and PRCs in these examples are obtained either from blood banks or from the American Red Cross Blood Services in New Jersey. Starting volumes in all examples is adjusted to about 450 mL. Leukocyte counting is done manually on influents and effluents using the well known chamber counting technique. Hematocrits are determined by the normal centrifugation method. Data is reported as average of two counts.

A separation device in accordance with the invention is assembled as follows:. A glass column measuring 3 cm internal diameter and 12 cm in height is stoppered at the bottom end with a one-holed rubber stopper containing an outlet tube having an internal diameter of 0.3 cm. A non-hemolytic porous polymeric frit (PVDF, POREX™), having a pore size of 25 μ, a thickness of 0.2 cm and a pore size rating of between 6.0 and 6.5 micrometers, is force fitted until it comes to rest on top of the rubber stopper. Spherical beads used in the column are purchased from vendors such as Pharmacia, Inc. The beads are of the hydrophilic, cross-linked agarose variety, and have well-known biocompatible characteristics.

A first layer of beads, SEPHAROSE™, CL-2 from Pharmacia Corp, having a diameter range of 20 to 30 micrometers is compacted onto the inserted frit to a height of 1 cm using the technique previously described in reference to FIG. 5. The average hydraulic diameter projected by these beads is between 8 and 12 micrometers. A second layer of beads SEPHAROSE™, CL-5 measuring approximately 50 micrometers in diameter is compacted over the first layer to a height of 3 cm. The third and topmost layer of beads SEPHAROSE™, CL-10 measured 100 micrometers in diameter, is added to a height of 5 cm., creating a total bed height of 9 cm. Another non-hemolytic frit, PVDF, POREX™, with an average pore size rating of between 80 and 90 micrometers is then force fitted onto the topmost bead layer. Finally, a second one-holed stopper with a similar inserted glass tube as the first one, is squeezed down until it rests on top of the porous frit. The device is flushed with sterile saline solution, and then sealed for use.

Using a microprocessor controlled pump (Cole-Parmer, Inc.) connected to the device assembly, a flow rate through the device of about 7 mL/minute is maintained. This flow rate corresponds to a flux of 1 mL/minute/cm$^2$ of cross-sectional flow area, or 1 cm/minute. This flow rate is at least 15-fold greater than prior art devices. Data shown in Table 1 indicates that at a minimum, the amount of leukocytes is reduced by about 4-logs (or 99.99%) for the most viscous feedstock(Examples 1–4), and about 5.3-log, i.e, 99.9995%) for the lowest viscosity feed stream(Examples 5–6). Whole blood averaged about 4.7-log removal efficiency. Red cell passage is high, with losses due to mechanisms other than entrapment being too small to be detected.

For comparison, two controls are performed. The first control employs a bottom porous member which has a large pore size (about 10 micrometers). The second control does not employ the bottom layer of beads. In the first control, removal efficiency dropped to about 3.5-log (99.97%). For the second control, separation efficiency varied between 1.2-log and 1.5-log (94%–97%). These results indicate that while the bottom two layers are effective in stripping the fluid stream of the final amounts of leukocytes, the intermediate layers play an important role in stratification of the bulk of the leukocytes. This verifies the surprising effects which the cascade pore structures and flow channels employed in the devices of the invention.

Microscopic analysis of the bead sections shows that between the top frit and the topmost bead layer, substantially all of the gel-like material and micro aggregates commonly found in blood, along with some leukocytes, are removed. The lower part of the top bead section, in conjunction with the middle section, retains the majority of leukocytes, with the lowest section able to strip the blood of leukocytes down to the final amounts. The lower frit effectively acts as a gatekeeper, showing preference towards passage of red cells.

TABLE 1

| Ex. No. | Feed Composition | Feed Vol. (mL) | Hematocrit (%) | Units Passed | Leukocyte Counts In Feed (No./mL) | Leukocyte Counts in Effluent (No./mL) | Log Removal | Removal Efficiency (%) |
|---|---|---|---|---|---|---|---|---|
| 1 | CPDA4 Blood | 440 | 49 | 1 | $3.4 \times 10^6$ | 108 | 4.5 | 99.997 |
| 1A[1] | CPDA-1 Blood | 425 | 49 | 2 | $3.1 \times 10^6$ | 123 | 4.4 | 99.996 |
| 2 | CPDA-1 Blood | 460 | 44 | 1 | $3.0 \times 10^6$ | 48 | 4.8 | 99.998 |
| 2A | CPDA-1 Blood | 430 | 44 | 2 | $2.8 \times 10^6$ | 56 | 4.7 | 99.998 |
| 3 | CPDA-1 PRC | 235 | 86 | 1 | $6.3 \times 10^6$ | 398 | 4.2 | 99.994 |
| 3A | CPDA-1 PRC | 220 | 86 | 2 | $5.7 \times 10^6$ | 718 | 3.9 | 99.987 |
| 4 | CPDA-1 PRC | 250 | 76 | 1 | $7.6 \times 10^6$ | 303 | 4.4 | 99.996 |
| 4A | CPDA-1 PRC | 245 | 76 | 2 | $6.5 \times 10^6$ | 410 | 4.2 | 99.994 |
| 5 | Adsol PRC | 320 | 63 | 1 | $2.3 \times 10^6$ | 23 | 5 | 99.999 |
| 5A | Adsol PRC | 315 | 63 | 2 | $2.4 \times 10^6$ | 48 | 4.7 | 99.998 |
| 6 | Adsol PRC | 365 | 55 | 1 | $2.0 \times 10^6$ | 10 | 5.3 | 99.9995 |
| 6A | Adsol PRC | 360 | 55 | 2 | $2.0 \times 10^6$ | 16 | 5.1 | 99.9992 |

[1]Use of the letter "A" after an experiment number indicates passage of a second unit of blood through the same device.

EXAMPLES 7–14

Affinity-enhanced, size-gradient leukocyte depletion to improve depletion levels of lymphocytes, neutrophils, granulocytes and monocytes Table 1 indicates the log removal obtained under non-enhanced, size-gradient conditions is as high as 5.1 and 5.3 (average 5.2). This is surprising since it shows an improvement of between 1 and 2 log over the prior art. However, experiments 7–14 are performed to show that removal of leukocytes can be further "enhanced" by affinity targeting to achieve a 6-log removal efficiency.

The size-gradient separation data from Examples 1–6 show that the layer of 100 micrometer beads, when combined with the layer of 50 micrometer beads of the 3 layer device employed in Examples 1–6, removes about 95% of the leukocytes on average. Therefore, enhancing separation in these two layers by using affinity ligands to achieved an additional 1-log removal in accordance with the invention is performed to achieve a cumulative separation effect of 6-log. The slurried volumes of 35 mL for the 100 micrometer-sized beads, and 21 mL for the 50 micrometer-sized beads as employed in Examples 1–6 are again used.

Several affinity ligands (or antibody molecules) specific to a range of leukocyte sub-types are commercially available through monoclonal antibody companies such as Becton Dickinson. Leukocytes vary widely in their state- and level of activation, distribution of cell adhesion molecules (CAMS) resident on the leukocytes which recognize the affinity ligand(s), age, buffer conditions, and so on. Consequently, one type of monoclonal antibody may be employed to produce desired effect, or a mixture of antibodies (polyclonals) may be employed. Antibody molecules can be attached to contacting surfaces of the separation devices of the invention through, for example, covalent linkage or physical adsorption. Covalent linkage is preferable when a level of permanency is desired. Physical adsorption is generally quicker, but less tenuous, and depends upon the fluid stream's chemical and/or flow conditions. For greatest adsorption to occur, hydrophobic contact surfaces are preferred for use in the separation device.

A useful hydrophobic contact surface is polystyrene. Smooth polystyrene beads of mean diameters of 100 microns (slurried volume 35 mL), and 50 microns (slurried volume 21 ml) are employed. The two bead sizes are maintained apart, and are not mixed together. Physical adsorption of antibody molecules to the beads is performed to equilibrium conditions as described by Hermanson, G. et al. (*Immob. Affinity Ligand Tech.,* Acad. Press, 1992). Two antibodies, anti-LECAM-1 and anti-Sialyl-Le$^x$, are employed. Anti-LECAM-1 is an antibody with specific reactivity for the L-selection antigen (MW 80 kD) found on lymphocytes and neutrophils; Anti-Sialyl-Le$^x$ is specific for the Sialyl-Lewis X antigen (MW 100–900 kD) found on granulocytes and monocytes. Since lymphocytes and neutrophils are small compared to monocytes and granulocytes, lymphocytes and neutrophils require smaller cascade channels than larger monocytes and granulocytes. The anti-LECAM-1 antibody therefore is adsorbed onto the 50 micrometer beads, while the anti-Sialyl-Lewis$^x$ antibody is adsorbed onto the 100 micrometer beads. The 100 micrometer beads present a larger surface area per bead than the 50 micrometer beads, thereby reducing the incidence of steric interaction. The beads are sandwiched in the columns between two porous, non-hemolytic polymeric frits as described previously, i.e., a 25 micrometer frit member at the bottom and a 80 micrometer frit member at the top. The packed height of the 50 micrometer beads is 3 cm and 5 cm for the 100 micrometer beads. All other experimental parameters such as flow rates, pump selection, and so on, are as before. Adsol-PRC is used as the low viscosity stream, and CPDA-1 PRC is used as the high viscosity feed stream. Controls consisted of the same beads, run under the same conditions, but without any affinity chemistry.

As shown in Table 2, the average log removal for the Adsol-PRCs is enhanced by 2.3 log over the corresponding control, while for CPDA-1 PRCs, the enhancement is 1.6 log. For Adsol, lower leukocyte counts and lower Hematocrits in the feed stream correlated to correlated to higher log removal efficiencies. For CPDA, higher removal efficiencies correlated inversely with leukocyte counts, but not with the hematocrit amounts in the feed stream. Without being bound by any theory, this could be due to the higher viscosity of the CPDA system, whereby a combination of laminar boundary-layer conditions and lowered convective transport of the relatively large leukocytes results in their not being brought to the affinity sites as efficiently as in the Adsol process.

TABLE 2

| Ex. No. | Feed Composition | Feed Vol. (mL) | Hematocrit (%) | Units Passed | Leukocyte Counts In Feed (No./mL) | Leukocyte Counts in Effluent (No./mL) | Log Removal | Removal Efficiency (%) |
|---|---|---|---|---|---|---|---|---|
| Control | Adosol PRC | 320 | 57 | 1 | $2.0 \times 10^6$ | $6.3 \times 10^4$ | 1.5 | 96.8 |
| 7 | Adsol PRC | 340 | 60 | 1 | $2.3 \times 10^6$ | 459 | 3.7 | 99.98 |
| 8 | Adsol PRC | 345 | 54 | 1 | $2.1 \times 10^6$ | 167 | 4.1 | 99.992 |
| 9 | Adsol PRC | 320 | 63 | 1 | $2.3 \times 10^6$ | 578 | 3.6 | 99.975 |
| 10 | Adsol PRC | 315 | 58 | 1 | $2.4 \times 10^6$ | 302 | 3.9 | 99.987 |
| | Average | | | | | | 3.83 | 99.984 |
| Control | CPDA-1 PRC | 240 | 86 | 1 | $5.8 \times 10^6$ | $3.4 \times 10^5$ | 1.2 | 94.1 |
| 11 | CPDA-1 PRC | 250 | 84 | 1 | $6.0 \times 10^6$ | 7553 | 2.9 | 99.87 |
| 12 | CPDA-1 PRC | 235 | 80 | 1 | $5.7 \times 10^6$ | 3596 | 3.2 | 99.94 |
| 13 | CPDA-1 PRC | 245 | 76 | 1 | $7.6 \times 10^6$ | $2.4 \times 10^4$ | 2.5 | 99.68 |
| 14 | CPDA-1 PRC | 240 | 78 | 1 | $6.5 \times 10^6$ | $1.0 \times 10^4$ | 2.8 | 99.84 |
| | Average | | | | | | 2.85 | 99.83 |

Calculations for determination of equilibrium binding constants, cell-to-surface binding densities, antibody-to-surface concentrations, cell monolayer thicknesses, and so on, can be found in any standard text book on adsorptive processes. Literature values for equilibrium binding constants of monoclonal antibodies for their antigens range from about $10^6$ to $10^{18}$ $M^1$, where the lower end reflects weaker binding, and the upper end, very high avidity. Values for my chosen antibody-antigen systems are $10^9$–$10^{11}$ $M^{-1}$, a range expected for leukocytes in various age groups, in different states and levels of antigen expression, and hampered to some extent by non-specific binding phenomena. Nevertheless, the spread in the log removal rate for Adsol-PRCs is relatively narrow, 0.5 log, compared to an enhancement of 2.3 logs; similar figures for CPDA-1 PRCs is 0.7 log on an enhancement over the control of 1.6 log. The antibodies are bound to the contacting surfaces at a concentration of approximately 1 $\mu g/cm^2$.

The data in Table 2 indicates that size-gradient leukodepletion, when combined with affinity techniques achieves high removal efficiencies. Cumulatively, overall log removals range from 5 to 7. The flexibility of the cascade separation devices of the invention permits various processes to be used in any combination with each other as desired. For example, a single-affinity stage with one or more cascading stages to obtain a desired degree of leukocyte removal, or, smaller amounts of monoclonal antibodies containing actual binding sites can be used as ligands to confer affinity. These monoclonal antibodies may be peptide ligands, typically from a few to several amino acids in length, or chemical ligands capable of mimicking binding site behavior.

EXAMPLE 15

Affinity-Enhanced Separation of Cells and Cellular Materials

In Examples 1–14, a graded, packed-bed technique to remove leukocytes from blood by interception, impingement and affinity removal mechanisms is used. In addition to these mechanisms, non-specific adsorption, or interaction between the leukocytes and the contacting surfaces, is also believed to affect separations. In applications where a particular subset of cells, or target particles need to be selectively retained and later eluted for other purposes, the method of the invention illustrated in Example 15 may be employed to remove leukocytes present in the blood, to attach target particles—*E. coli* cell-debris with entrapped beta-galactosidase as the marker enzyme for later elution, and to permit passage of the red blood cells.

In Example 15, the enzyme beta-galactosidase for a substrate analog called para-aminobenzyl-1-thio-β-D-galactopyranoside (PABTG) is used as the ligand. *E. coli* bacteria constitutive for beta-galactosidase are grown in minimal media on glycerol as per previously established protocols (Datar, R., *Ph.D. Thesis*, Royal Institute of Technology, Stockholm 1986). Beta-galactosidase is expressed in substantial quantities and collects in an area of the bacterial cell wall known as the periplasmic space sandwiched between the two layers that form the bacterial cell wall. When the bacteria so grown are fresh, there is almost no leakage of the enzyme to the outside fermentation medium. The fermentation medium is spun down in a conventional centrifuge, the cells washed twice with phosphate buffered saline (PBS), and resuspended in PBS. No enzyme could be detected in the resuspended medium. The cells are ruptured by sonication.

Whole *E. coli* are cylindrical in shape and typically measure 1.2 $\mu$m×0.6 $\mu$m. Disrupted *E. coli* cells, measure about 0.1–0.3 $\mu$m depending upon the degree of breakage. Disruption is deemed complete when no further increases in enzyme activity can be detected. The suspension then is spun down in a centrifuge. Intact cells are found compacted at the bottom of the centrifuge tube below a layer of cell debris. The cell debris is separated by decantation, centrifuged and washed twice in PBS, and resuspended in fresh buffer. By measuring enzymic activity levels in the medium vs. the washed cell debris suspension, it is concluded that the cell debris has quantities of beta-galactosidase attached to the debris, while the amounts released to the medium are below the levels of detection.

The cell debris with attached beta-galactosidase is then added to 200 ml of whole human heparinized blood at 4° C. The PABTG/Agarose affinity adsorbent complex is from Sigma Chemical Co. (St. Louis, Mo.). PABTG can also be covalently attached to agarose beads of any desired size as per established procedures and protocols (Hermanson, G. et al.) as described above. The kinetics of binding are similarly determined by reference to standard text books on chromatography (e.g., Sofer, G. et al., Practical Chromatography, Wiley, 1989).

A separation device with low aspect ratio such as shown in FIG. 6 is assembled as below. A 2 millimeter thick polyethylene filter membrane with an average pore size of about 7 micrometers is placed in a stainless steel housing of 47 millimeter diameter. PABTG-agarose particles are then compacted onto the bottom porous polyethylene filter membrane to a thickness of about 5 millimeters. Another membrane with pore size rating of 40 micrometers is placed above the agarose particles. Next, a 10 millimeter layer of solid polystyrene beads 50 micrometers in diameter and with a polyhydroxyl gel coating is compacted onto the second membrane sheet. Finally, a third membrane sheet of 40 micrometer pore size is placed above the polystyrene beads. The lid of the housing is then placed in position and tightly clamped down to stop any leaks from the sides of the device.

Flow of blood suspension (250 ml) is maintained at 1 ml/minute/cm² through the device from the port with the most open membrane sheet (top). This flow rate is aided by a microprocessor controlled peristaltic pump. Effluent exiting at the bottom of the device contains a majority of red blood cells with a negligible amount of leukocytes. No bacterial cell debris or its associated marker enzyme beta-galactosidase could be detected in the effluent. The blood is chased with a flow of PBS to wash out loosely bound particles. The direction of flow then is reversed at the same flow rate for a period of time sufficient to dislodge some loosely bound particles. The flow rate is slowly increased to 3 cm/minute, the effluent exiting from the top of the device is monitored and samples drawn. When the effluent stream appears clear, flow is reversed once again, and a PBS chase performed at 1 cm/minute for a few minutes. Desorption of the adsorbed beta-galactosidase/cell-debris complex is accomplished by introduction of borate ions (0.1 M, pH 9.0 sodium borate), the borate ions complex with free hydroxyl groups on the ligand (PABTG) and thus compete with beta-galactosidase for adsorption sites. Samples of effluent are drawn from the bottom portion of the device. All samples are analyzed. Mass balance calculations show that within experimental error, almost all of the enzyme activity is recovered. The data is shown in Table 3.

The devices and processes of the invention thus may be used for therapeutic and diagnostic applications. For example, monoclonal antibodies are finding increasing uses because of their ability to specifically attract and attach to target particles such as cells, viruses, proteins, and the like. However, highly purified monoclonal antibodies are extremely expensive, a few milligram quantities typically costing thousands of dollars. Thus, the present invention which is surprisingly able to combine size-gradient separation with affinity adsorption, has the dual ability to minimize the requirements for monoclonal antibody usage while producing high recoveries and yields.

not rejected by the immune system when transplanted into humans. It has been recently discovered that most of the human antibodies against porcine xenograft transplants are directed towards a carbohydrate antigen (Sandrin, M., Proc. Natl. Acad. Sci., Vol 90, p. 11391–5, December 1993). Humans have natural IgM antibodies to pig cells. This triggers an almost immediate, or hyperacute, rejection of the foreign tissue. Past studies have shown that by removing the cell membranes containing such carbohydrate antigens from porcine and other mammalian organs, human IgM antibodies failed to react with the tissues. Studies additionally have indicated that these human antibodies react with monosaccharides such as galactose, α-D-galactopyranoside, melibiose, and the like, showing immunogenicity to the α linkages but not to the β configuration. Consequently, one approach to delay, if not avert, rejection would be to use α-galactose type sugars to remove the circulating IgM antibodies either prior to a xenotransplant, or as part of post-operative procedure and maintainence.

A concern generally related to plasmapheresis, transfusions, and transplants is the ability to process platelets efficiently. The normal technique used for separating various cells from blood is centrifugation. However, centrifugation is inefficient for concentrating platelet fractions.

The previous examples demonstrated the ability of the invention to separate and/or remove cell various fractions. In Examples 16–24, a process is provided to simultaneously remove rejection antibodies, to reduce leukocyte counts, and to enable red cells and platelets to pass through.

In Examples 16–24, CPDA-1 Whole Blood is used. Three ligands (Sigma Chemical Co., St. Louis) are tested for their effectiveness in attaching to the IgM molecule. The first ligand is melibiose; the second, para-aminophenyl α-D-galactopyranoside (PAP-α-G); and the third, para-aminobenzyl-1 -thio-α-D-galactopyranoside (PABT-α-G). All three ligands are characterized by the α-galactose structure as against the β configuration, and are attached to cross-linked, beaded agarose particles of diameter 500 μm through divinyl sulfone-, p-nitrophenyl chloroformate-, and cyanogen bromide activation, respectively. A key difference

TABLE 3

| STEP | Influent | | | | Effluent* | | | |
|---|---|---|---|---|---|---|---|---|
| | WBC[1] 10⁶/mL | RBC[2] (% v/v) | beta-gal[3] Activity (IU/mL) | beta-gal Purity** (IU/mg) | WBC Cum. Rec.*** (%) | RBC Cum. Rec. (% v/v) | beta-gal Activity (IU/mL) | beta-gal Purity (IU/mg) |
| FEED**** | 2400 | 47 | 45 | 0.51 | | | | |
| Load | | | | | 3 | 92 | 4.5 | — |
| PBS wash | | | | | — | — | 2.2 | — |
| Flow reversal | | | | | 96 | 94 | B.D. | — |
| PBS wash | | | | | — | — | B.D. | — |
| Flow reversal & Elution | | | | | — | — | 32 | 864 |
| YIELD | | | | | 96 | 95 | 70% | 96% |

Notes:
*Effluent stream may be at top or bottom of device depending upon step being performed.
**Purity of beta-galactosidase as purchased form Sigma Chemicals: approx. 900 IU/mg protein.
***Cumulative recovery. RBC's determined by spin-down test.
****Feed start volume: approx. 200 mL; total protein concentration: approx. 17,600 mg.
[1]White Blood cell
[2]Red Blood cell
[3]Beta galactosidase EXAMPLES 16–24
Removal of Antibodies Xenograft transplant concerns use of animal organs such as those obtained from pigs for transplantation into humans. A long-term goal in xenotransplantation research is to genetically modify the transplant organ so that the organ is between the three ligands is the length of the spacer arm used: 5 atoms for melibiose; 1 atom for PAPG; and 12 atoms for PAPTG. IgM molecules are pentameric, and can exist in size up to 900,000 Daltons, creating the possibility of severe steric hindrance. Attaching the ligands to large beads which provide a relatively large surface area can reduce the effects of steric interaction. Because the affinity is for the IgM molecule, some leukocytes may adhere to the ligands via the Sialyl-Lewis X antigens resident on those leukocytes. This effect could enhance removal of those particular leukocytes. However, leukocytes can be large, particles and their transport to contacting surfaces thus would be governed by convection rather than diffusion. Since the flow of fluid between beads is laminar, mass transfer can be expected to be diffusion-limited. Should convective transport be desired, ligand(s) can be attached to multiple layers of high-porosity, high surface area microporous sheets or membranes which contain projections and/or ribs as described in FIG. 10, FIG. 10A and FIG. 10B, and used in device of FIG. 10C. By selection of the pore size cascade as described above, it is possible to permit or restrict the entry of various cellular fractions present in blood.

For reduction of leukocytes, a bead cascade of the type in Example 1 is utilized. Pooled pre- and post-device samples are collected for analysis, and reported as the average of paired samples. The control consists of 500 μm agarose beads without the ligand attached. IgM levels are estimated by the known non-reducing Polyacrylamide Gel Electrophoresis (PAGE) technique, chosen so as not to dissociate the large IgM molecule into its monomers, stained with Coomassie Blue, and laser-scanned for relative quantification in a Molecular Dynamics Personal Gel Scanner. Platelet behavior is determined through the following measurements: platelet count; beta-thromboglobulin (BTG) activity as being indicative of level of platelet activation; and, intra-platelet serotonin levels to establish whether the platelets are functional.

A device of aspect ratio 10 (1 cm. dia.×10 cm. height.) is used. The bottom porous frit and the three adjacent bead layers are identical to that of Example 1. However, the top-most bead layer is 500 μm beads with, or without the ligands, depending upon the particular experiment. The trials are performed as per flow conditions previously established.

Results in Tables 4 through 6 show the effectiveness of a combined affinity-size gradient technique to achieve the simultaneous goals of acceptable levels of antibody removal; leukocyte reduction; and platelet and red cell passage, while largely maintaining platelet function.

TABLE 4

| Ex. No. | Relatve IgM Level Pre Separation | Relative IgM Level Post Seperation | Leukocyte Removal (log) | Red Cell Recovery (%) | Platlets Pre-Separation | Platlets Post Separation[1] | Platelets Recovered (%) |
| --- | --- | --- | --- | --- | --- | --- | --- |
| Control[2] | 1 | 0.82 | 4.4 | 90 | $68 \times 10^3$ | $40 \times 10^3$ | 59 |
| 16 | 1 | 0.50 | 4.6 | 88 | $62 \times 10^3$ | $35 \times 10^3$ | 57 |
| 17 | 1 | 0.45 | 4.8 | 86 | $94 \times 10^3$ | $61 \times 10^3$ | 65 |
| 18 | 1 | 0.50 | 4.6 | 89 | $46 \times 10^3$ | $27 \times 10^3$ | 59 |
| Average | | 0.48 | 4.67 | 87.7 | | | 60 |

[1]Ligand = Melibiose
[2]Control does not have ligand

TABLE 5

| Ex. No. | Plasma BTG Level Pre Separation | Plasma BTG Level Post Separation | % Change | Intraplatelet Serotonin Level Pre Separation[3] | Intraplatelet Serotonin Level Post Separation[3] | % Change |
| --- | --- | --- | --- | --- | --- | --- |
| Control[1] | 32 (ng/ml)[2] | 50 (ng/ml) | 56% | 240 | 236 | −2% |
| 19 | 44 | 55 | 25 | 190 | 194 | −3 |
| 20 | 92 | 124 | 35 | 86 | 75 | −13 |
| 21 | 26 | 31 | 20 | 237 | 195 | −18 |
| Average | | | 27 | | | −11 |

[1]Control does not have ligand
[2]Normal range is 24–28 ng/ml
[3]Normal range is 350–950 ng/$10^9$ platelets

TABLE 6

| Ex. No. | Relative IgM Level Pre Separation | Relative IgM Level Post Separation[2] | Relative IgM Level Pre Separation | Relative IgM Level Post Separation[3] | Relative IgM Level Pre Separation | Relative IgM Level Post Separation[4] |
| --- | --- | --- | --- | --- | --- | --- |
| Control[1] | 1 | 0.86 | 1 | 0.86 | 1 | 0.86 |
| 22 | 1 | 0.54 | 1 | 0.76 | 1 | 0.18 |
| 23 | 1 | 0.48 | 1 | 0.72 | 1 | 0.15 |
| 24 | 1 | 0.56 | 1 | 0.73 | 1 | 0.16 |
| Average | | 0.53 | | 0.74 | | 0.16 |

[1]Control does not have ligand
[2]Ligand = Melibiose
[3]Ligand = PAP G
[4]Ligand = PABT G

EXAMPLES 25–26

In Examples 25–26, preparation of reagents, DNA solutions, analytical methods and the like are performed according the procedures in Sambrook et al., Molecular Cloning: A Laboratory Manual, 2nd Ed., Cold Spring Harbor Laboratory Press, Cold Spring Harbor, N.Y., 1989; and the SpinBind® Instruction Manual. The DNA fragments used are purchased from vendors of molecular biology products such as Sigma Chemical Co., and Aldrich Chemical Co.

A separation device of low aspect ratio of about 0.1 is constructed as described below. A porous frit of 20 mm diameter and 2 μm pore size (Porex®) is placed in a holder, the underneath portion of which is attached to a vacuum source. A slurry of silica particles of about 5 μm diameter size is pipetted onto the top portion of the frit and a vacuum drawn from underneath. Pipetting of the slurry is stopped when the thickness of the resulting layer is about 2 mm. Another porous frit having a pore size of about 5 μm then is compressed onto the silica cake by simultaneous application of vacuum from underneath and pressure from above. Alternative materials in and on which layers or coatings can be created include Amer-Sil MPS™, BioPor(BPS) from Synosys, Jungfahr(Austria), or Entek(Entek Cookson,UK).

Application of reagents, DNA solutions(4,000 μL), DNA binding, wash procedures, and the like are performed as per art recognized protocols(See Sambrook et al., Molecular Cloning: A Laboratory Manual, 2nd Ed., Cold Spring Harbor Laboratory Press, Cold Spring Harbor, N.Y., 1989), but with two exceptions. Normally in the art, the wash and elution steps of bound DNA are performed in the same flow direction as the application step. In the present examples of the invention, however, the wash and the elution steps are performed in the reverse direction. Since the device of the invention employs a cascaded flow channel, the wash step permits substantially complete removal of contaminates which may be trapped in the matrix, while elution enables substantially all bound DNA to leave the matrix. This aspect of the invention thus achieves high purity of recovered DNA, as well as high recovery efficiencies. The data is shown in Table 7.

TABLE 7

| | Recovery of DNA (%)[1] | | | | | | | | |
|---|---|---|---|---|---|---|---|---|---|
| | DNA Base Pairs[2] | | | | | | | | |
| Ex. | 0.02 | 0.3 | 0.5 | 2 | 6 | 9 | 23 | 30 | 50 |
| 25 | 93.20% | 90.02% | 89.2% | 91.4% | 94.8% | 84.2% | 79.8% | 74.0% | 61.2% |
| 26 | 102[3] | 98.00 | 97.2 | 852 | 90.00 | 89.9 | 74.8 | 68.3 | 55.8 |
| Ave. Recovery | 98% | 94% | 93% | 88% | 92% | 87% | 77% | 71% | 59% |
| Std. Dev. | 6.22% | 5.52% | 5.66% | 4.38% | 3.39% | 4.03% | 3.54% | 4.03% | 3.82% |

[1] Quantification of DAN performed as per the ethidium bromide spotting technique of Sambrook et al., Molecular Cloning: A Laboratory Manual, 2nd Ed., Cold Spring Harbor Laboratory Press, Cold Spring Harbor, NY, 1989
[2] (kilobases, kb)
[3] Due to inherent errors in the measurement technique While Examples 25–26 are performed to recover DNA from solutions, this invention is not limited to such, and is applicable to, for example, purification of DNA, RNA and other fragments from agarose gels, Polymerase Chain Reaction(PCR) solutions and the like.

It is evident from the above that the invention has a wide variety of applications such as therapy and diagnostics. Although the invention has been described in detail by way of illustration and example for purposes of clarity and understanding, it is understood that within various modifications within the scope of the appended claims, as well as certain changes and modifications may be practiced.

What is claimed is:

1. A process for separating one or more target components from a fluid mixture comprising,
    passing a fluid mixture having one or more target components therein in a first direction through a separation media containing a plurality of porous membranes and graded particulates having increasingly smaller diameters to create a cascading flow channel through progressively smaller pore sizes and interstices between the particulates in the first direction, for separating said one or more target components from said fluid mixture, wherein said fluid mixture passes through at least one of said porous membranes and then through said graded particulates.

2. The process of claim 1 wherein said graded particulates are beads selected from the group consisting of polymeric beads, non-polymeric beads, and mixtures thereof, and said porous membranes comprise at least one of polymeric membranes, non-polymeric membranes, or combinations thereof.

3. The process of claim 2 wherein said beads are chemically treated with chemical moieties, said moieties having affinities for said target components.

4. The process of claim 3 wherein said separation media comprises a layer of beads positioned between two of said porous membranes, each of said porous membranes having approximately equal pore sizes.

5. The process of claim 4 wherein said porous membranes are piezoelectric membranes.

6. The process of claim 3 wherein said separation media comprises a layer of beads positioned between two of said porous membranes, each of said porous membranes having different pore sizes.

7. The process of claim 3 wherein said separation media comprises multiple layers of said beads alternating with multiple layers of said porous membranes.

8. The process of claim 3 wherein at least one of said porous membranes is bonded to a porous metal support.

9. The process of claim 1 wherein said separation media comprises at least one of polymeric materials and non-polymeric materials bonded to metals.

10. The process of claim 1 wherein said fluid mixture includes three target components wherein two of said three target components are removed from said fluid mixture and one of said three target components is increased in purity during said separating.

11. The process of claim 10 wherein said two of said three target components are rejection antibodies and leucocytes, and said one of said three target components is red blood cells.

12. The process of claim 1 wherein said separation media comprises first, second and third layers of beads, wherein said beads in said first layer have an average diameter of about 100 microns, said beads in second layer have an average diameter of about 50 microns, and said beads in said third layer have an average diameter of about 20–30 microns, and wherein said fluid mixture flows in said first direction successively through said first layer, said second layer and said third layer.

13. The process of claim 12 wherein flux generated during flow of said fluid mixture through said separation media is about $1 ml/minute/cm^2$.

* * * * *